United States Patent [19]

Hyatt et al.

[11] 4,281,143

[45] Jul. 28, 1981

[54] PROCESS FOR PREPARING 1-ARYL-3-AMINO-5-PYRAZOLONES

[75] Inventors: John A. Hyatt, Kingsport, Tenn.; Stephen E. French, Rochester; Cataldo A. Maggiulli, Pittsford, both of N.Y.

[73] Assignee: Eastman Kodak Company, Rochester, N.Y.

[21] Appl. No.: 72,548

[22] Filed: Sep. 4, 1979

[51] Int. Cl.$^3$ .................................. C07D 231/52
[52] U.S. Cl. .................................................. 548/360
[58] Field of Search ....................................... 548/360

[56] References Cited

U.S. PATENT DOCUMENTS

| 2,983,608 | 5/1961 | Beavers | 430/562 |
|---|---|---|---|
| 3,931,221 | 1/1976 | Meier et al. | 548/360 |
| 3,956,311 | 5/1976 | Kuffner et al. | 548/360 |
| 3,979,412 | 9/1976 | Arai et al. | 548/360 |

OTHER PUBLICATIONS

Jerchel, Chem. Abst. 1958, vol. 52, p. 11919 h, (Abst. of Ger. 884,368).

*Primary Examiner*—Henry R. Jiles
*Assistant Examiner*—Natalia Harkaway
*Attorney, Agent, or Firm*—Donald W. Spurrell; Daniel B. Reece, III

[57] ABSTRACT

Disclosed is a process for the preparation of certain 1-aryl-3-amino-5-pyrazolones by reacting a 3-nitropropionic acid ester with certain aryldiazonium salts to produce intermediate α-nitrohydrazones and then reducing the intermediate to give the corresponding aminopyrazolones. The aryl group may be, for example, phenyl, 4-methoxyphenyl, or the like, the diazo anion can be, e.g., $Br^-$, $Cl^-$, $BF_4^-$, or $SO_4^=$, and the ester alcohol moiety can be any convenient, unreactive group, preferably alkyl. The aminopyrazolones are useful for the preparation of photographic couplers.

5 Claims, No Drawings

PROCESS FOR PREPARING 1-ARYL-3-AMINO-5-PYRAZOLONES

The present invention concerns a process for the preparation of 1-aryl-3-amino-5-pyrazolones by reacting a 3-nitropropionate such as an alkyl-3-nitropropionate, e.g., ethyl, with certain aryldiazonium salts to produce the intermediate α-nitrohydrazones and then reducing (preferably catalytically) the intermediate to give the corresponding aminopyrazolones. The aryl group may be, for example, phenyl or 4-methoxyphenyl, and the diazo anion can be $Br^-$, $Cl^-$, $BF_4^-$, $SO_4^=$ or the like. The aminopyrazolones are useful for the preparation of photographic couplers.

Prior art processes for the preparation of such pyrazolones involve, for example, the reduction of aryldiazonium salts to the arylhydrazines, which are then used to prepare the 1-aryl-3-amino-5-pyrazolones by reaction with alkyl-3-alkoxy-3-iminopropanoates. This procedure is not useful however in a great many instances since it leads to substantial by-product formation and non-purifiable product.

The present procedure is depicted as follows:

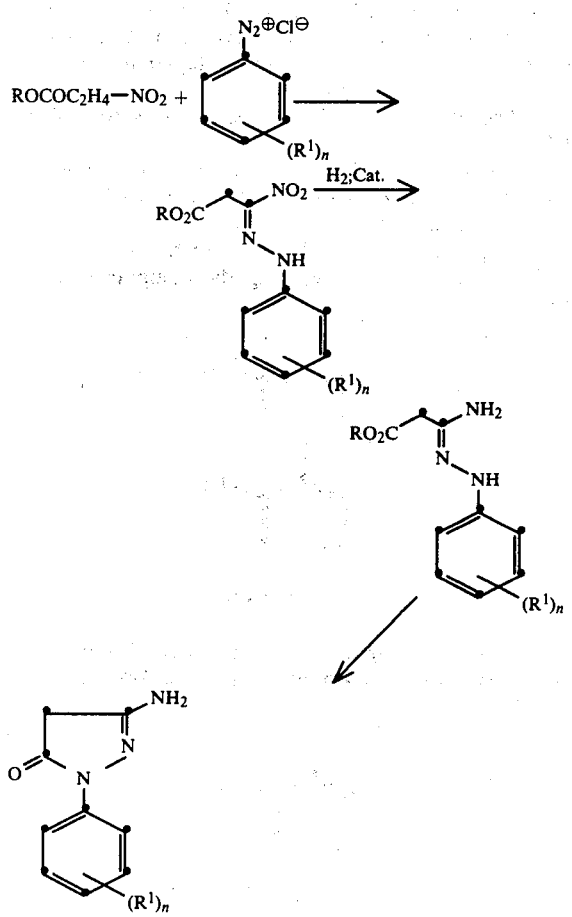

wherein R is any radical which does not react under the process conditions and includes alkyl, cycloalkyl, aryl, various heterocycles, and the like typified by methyl, ethyl, hexyl, cyclohexyl, phenyl, thiazole, benzothiazole, thiophene, and such radicals bearing non-reactive substituents. Preferably R is straight or branched alkyl of 1-8 carbons; each $R^1$ is independently selected from hydrogen, lower dialkylamino; and straight or branched lower alkyl, lower alkoxy, phenyl and cyclohexyl, each of which may be substituted with hydroxy, lower alkoxy, or lower dialkylamino; and n is 1, 2 or 3. The term "lower" as used herein means 1-6 carbons.

The present invention is defined as the process for preparing 1-aryl-3-amino-5-pyrazolones of the formula

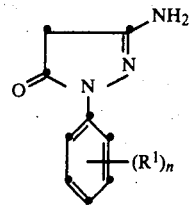

comprising reacting a 3-nitropropionate with an aryldiazonium salt of the formula

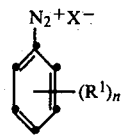

to produce the intermediate α-nitrohydrazones, and then reducing said intermediate to give the corresponding aminopyrazolones, wherein each $R^1$ is independently selected from hydrogen; lower dialkylamino; and straight or branched lower alkyl, lower alkoxy, phenyl and cyclohexyl, each of which may be substituted with hydroxy, lower alkoxy, or lower dialkyl amino n is 1, 2 or 3; and X is an anion.

In carrying out the process the arylamine such as aniline is diazotized in conventional manner, e.g., $HCl + NaNO_2$ in water, and the solution then admixed with the nitro ester and base to give a substantially neutral system at low temperature, e.g., below about 5° C. The resulting hydrazone may be isolated and purified prior to reduction, or the reduction may be carried out in the reaction mixture. The reduction may be done in conventional manner, e.g., with #28 Raney nickel at 40° C. and 40 psi $H_2$ for six hours. The cyclization to the pyrazolone is essentially spontaneous upon reduction. Other known and useful reducing systems are shown, for example, in the texts, *Catalytic Hydrogenation*, Robert L. Augustine, 1965, Marcel Dekker, Inc., and *Catalytic Hydrogenation Over Platinum Metals*, Paul N. Rylander, 1967, Academic Press.

The nitropropionates may be prepared, for example, as follows:

A twelve liter, 3-necked flask was charged with 100 g. urea, 283 g. sodium nitrite, and 1.5 l. dimethylformamide. After stirring for 1.5 hr. at 25° C., 300 g. ethyl-3-bromopropionate was added over 1 hr., and the mixture stirred an additional 2.5 hrs. The temperature rose to 37° C., and the mixture darkened considerably. The mixture was diluted with 8.0 l. of water and extracted six times with 300 ml. of dichloromethane. The extract was dried ($MgSO_4$) and stripped of $CH_2Cl_2$ and by-product ethyl acrylate at reduced pressure, and the residue distilled, bp 70°–75° (5 mm) and then redistilled (16 in. vigreaux, bp 95°, 9 mm) to give 58.8 (24% yield) of ethyl-3-nitropropionate.

The following examples will further illustrate the invention.

EXAMPLE 1—Ethyl-3-Nitro-3-(Phenylhydrazono)propanoate

A stirred mixture of aniline (4.65 g., 0.05 mole), concentrated HCl (12 ml.) and water (28 ml.) was cooled to <5° C. and treated with a 5° C. solution of sodium nitrite (3.5 g., 0.05 mole) in water (10 ml.). After 0.5 hr., this diazonium solution was added to a 0°–5° C. solution of the above nitro ester (7.34 g., 0.05 mole) in ethanol (100 ml.) containing sodium metal (2.5 g., 0.11 mole) dissolved. The coupling mixture was let warm to 25° C., diluted with water (100 ml.) and the yellow solid product filtered off. Yield, 10.6 g. (74.4%) of product pure by TLC and NMR. An analytical sample recrystallized from ethanol had a mp. of 107°–109° C. Similarly prepared are ethyl-3-nitro-3-(4'-methoxyphenylhydrazono)propanoate and ethyl-3-nitro-3-(2'-methoxy-5'-acetamidophenylhydrazono)propanoate).

EXAMPLE 2—1-Phenyl-3-Amino-5-Pyrazolone

A solution of 1.0 g. of the above ethyl-3-nitro-3-(phenylhydrazono)propanoate in 75 ml of methanol was treated with 0.3 g. #28 Raney nickel and hydrogenated at about 40° C. and about 40 psi $H_2$ for 6.0 hrs. The mixture was filtered (celite) and the filtrate evaporated to give a green gum. The gum was dissolved in $CHCl_3$ and eluted through a Florisil column (50 g. Florisil, 5% $CH_3OH$ in $CHCl_3$ elution) to give 0.52 g. (74.7%) pure tan solid.

EXAMPLE 3—1-(p-Methoxyphenyl)-3-Amino-5-Pyrazolone

A mixture of ethyl-3-nitro-3-(4'-methoxyphenylhydrazono)-propanoate (0.5 g.), methanol (70 ml.) and 0.3 g. #2 Raney nickel was hydrogenated at 40° C. and 40 psi $H_2$ for 6 hrs. The resulting mixture was filtered (celite), evaporated, and the dark residue chromatographed on Florisil (50 g.; 5% MeOH in $CHCl_3$ elution) to give after recrystallization from methanol 0.31 g. tan solid, mp 191°–192° dec, yield, 43%.

The invention has been described in detail with particular reference to certain preferred embodiments thereof, but it will be understood that variations and modifications can be effected within the spirit and scope of the invention.

We claim:

1. The process for preparing a 1-aryl-3-amino-5-pyrazolone of the formula

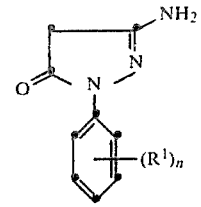

comprising reacting a non-reactive ester of 3-nitropropionic acid with an aryldiazonium salt of the formula

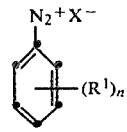

to produce the intermediate α-nitrohydrazone, and then reducing said intermediate to give the corresponding aminopyrazolone, wherein each $R^1$ is independently selected from hydrogen; lower dialkylamino; and straight or branched lower alkyl, lower alkoxy, phenyl and cyclohexyl, each of which may be substituted with hydroxy, lower alkoxy, or lower dialkylamino; n is 1, 2 or 3; and X is an anion.

2. The process of claim 1 wherein X is $Br^-$, $Cl^-$, $BF_4^-$, or $SO_4^=$.

3. The process of claim 1 wherein the ester is ethyl-3-nitropropanoate, $R^1$ is 4-methoxy, and X is $Cl^-$.

4. The process of claim 1 wherein the ester is ethyl-3-nitropropanoate, $R^1$ is hydrogen, and X is $Cl^-$.

5. The process for preparing the compound of the formula

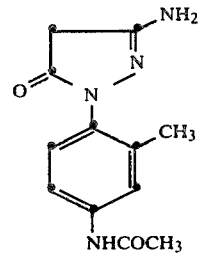

comprising reacting a nonreactive ester of 3-nitropropionic acid with a diazonium salt of the formula

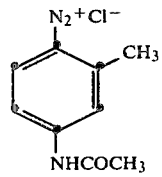

to produce the intermediate α-nitrohydrazone, and then reducing said intermediate to give the corresponding aminopyrazolone.

* * * * *